United States Patent [19]

Garsky

[11] 4,159,263

[45] Jun. 26, 1979

[54] (D-ALA⁵)-SOMATOSTATIN AND ANALOGUES THEREOF

[75] Inventor: Victor M. Garsky, Radnor, Pa.

[73] Assignee: American Home Products Corporation, New York, N.Y.

[21] Appl. No.: 795,685

[22] Filed: May 11, 1977

[51] Int. Cl.² .................... C07C 103/52; A61K 37/00
[52] U.S. Cl. .............................. 260/112.5 S; 424/177
[58] Field of Search .................. 260/112.5 S; 424/177

[56] References Cited

U.S. PATENT DOCUMENTS 4,062,816  12/1977  Shields ........................... 260/112.5 S

OTHER PUBLICATIONS

J. Rivier, et al., Biochem. and Biophys. Res. Commun., 65, 1975, pp. 746-750.

*Primary Examiner*—Delbert R. Phillips

*Attorney, Agent, or Firm*—Arthur G. Seifert

[57] ABSTRACT

Polypeptides of the formula:

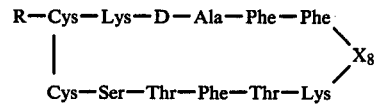

wherein:
R is hydrogen, lower alkanoyl, Ala-Gly-, Gly-Gly-Gly-, Ala-D-Ala- or p-Glu; and
$X_8$ is L-Trp or D-Trp;

or the linear reduced form thereof; or a nontoxic acid addition salt thereof; are described. (D-Ala)⁵-Somatostatin and its analogues inhibit the release of growth hormone and insulin without materially affecting the secretion of glucagon, and are useful in the treatment of hyperinsulinemia and acromegaly.

2 Claims, No Drawings

(D-ALA⁵)-SOMATOSTATIN AND ANALOGUES THEREOF

Somatostatin is the cyclic disulfide tetradecapeptide of the formula:

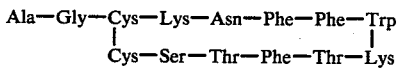

This peptide (I) has been identified as the "somatotropin-release inhibiting factor" (SRIF) which is secreted by the hypothalamus and regulates the secretion of pituitary growth hormone (GH) (somatotropin). [See Brazeau, et al., *Science*, 179, 77 (1973), Burgus, et al., *Proc. Nat. Acad. Sci. (U.S.A.)*, 70, 684 (1973), and Ling, et al., *Biochemical and Biophysical Res. Communication*, 50, 127 (1973)]. The reduced form of somatostatin (RS) is the linear tetradecapeptide of the formula:

The reduced form (II) hs been prepared by total synthesis, [see Rivier, et al., *C. R. Acad. Sci. Ser. p. Sci. Natur.* (Paris), 276, 2737 (1973) and Sarantakis and McKinley, *Biochem. and Biophys. Res. Communications*, 54, 234 (1973)] and it (II) can be converted to somatostatin (I) by oxidation whereby a bridging bond is formed between the two sulfhydryls of the two cysteinyl amino acid residues in the tetradecapeptide.

The present invention relates to novel synthetic polypeptides which have biological activity and which may be characterized as a chemical modification of somatostatin or reduced somatostatin.

In particular this invention comprises polypeptides of the formula:

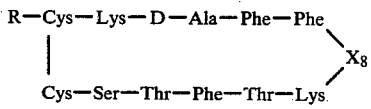

wherein:
R is hydrogen, lower alkanoyl, Ala-Gly-, Gly-Gly-Gly-, Ala-D-Ala-, or p-Glu; and
$X_8$ is L-Trp or D-Trp;
or a non-toxic acid addition salt thereof. In addition, the invention contemplates the linear form of the compounds of Formula III (i.e. the non-cyclic reduced compounds which contain two free sulfhydryl groups), or a non-toxic acid addition salt thereof.

When R in the compounds of Formula III is Ala-Gly-, the compounds may be characterized as (D-Ala⁵)-somatostatin, when $X_8$ is L-Trp, or as (D-Ala⁵, D-Trp⁸)-somatostatin, when $X_8$ is D-Trp.

All optically active amino acid residues in the polypeptides of Formula III and the other polypeptides herein described are in the natural or L-configuration, unless otherwise indicated.

The compounds of Formula III and the linear reduced form thereof inhibit the secretion of growth hormone and insulin without materially affecting the secretion of glucagon, and, therefore, are useful in the treatment of pathologic conditions characterized by the hypersecretion of growth hormone and/or insulin.

The polypeptides of this invention are produced by the well known solid phase method as described by Stewart et al., Solid Phase Peptide Synthesis, Freeman and Co., San Francisco, 1969. As applied to the compounds of this invention, α-amino and sulfhydryl protected cysteine is attached to a chloromethylated polystyrene resin followed by removal of the α-amino protecting group with trifluoroacetic acid in methylene chloride, trifluoroacetic acid alone or hydrogen chloride in dioxane. The deprotection is conducted at a temperature between about 0° C. and room temperature. Other standard cleaving reagents and conditions for removal of specific α-amino protecting groups may be used as described in Schroder E. Lubke, "The Peptides", 1, 72–75 (Academic Press, 1965). After removal of the α-amino protecting group the subsequent protected amino acids are coupled individually to the resin supported sequence, seriatim. Alternatively, small peptide fragments may be prepared by the solution method and introduced into the solid phase reactor in the desired order. Each protected amino acid or amino acid sequence is introduced into the solid phase reactor in about a four fold excess. The coupling is carried out in dimethylformamide, methylene chloride, or a mixture of the two solvents. The success of each coupling reaction at each stage of the synthesis is determined by the ninhydrin reaction as described by E. Kaiser et al., *Analyt. Biochem.*, 34, 595 (1970). Where incomplete coupling has occurred, the reaction is repeated before the α-amino protecting group is removed for introduction of the next amino acid or amino acid sequence. The coupling reagents employed were N-hydroxybenzotriazole and dicyclohexylcarbodiimide.

After the desired amino acid sequence has been synthesized, the polypeptide is removed from the resin support by treatment with hydrogen fluoride and anisole to obtain the fully deprotected linear polypeptide. The cyclic disulfide is produced by air oxidation.

Non-toxic acid addition salts of the linear and cyclic polypeptides are produced by methods well known in the art from hydrochloric, hydrobromic, sulfuric, phosphoric, polyphosphoric, maleic, acetic, citric, benzoic, succinic, malonic, or ascorbic acid and the like.

The protecting groups employed throughout the solid phase synthesis are well known to the art. In selecting a particular side chain protecting group to be used in the synthesis of the peptides of this invention, the following rules should be followed: (a) the side chain protecting group must be stable to the reagent and under the reaction conditions selected for removing the α-amino protecting group at each step of the synthesis, (b) the protecting group must retain its protecting properties (i.e. not be split off under coupling conditions), and (c) the side chain protecting group must be removable upon the completion of the synthesis containing the desired amino acid sequence under reaction conditions that will not alter the peptide chain.

The following Examples illustrate the preparative techniques applicable in the production of the compounds of the invention. By introducing tert-butyloxycarbonyl protected L-tryptophan into the solid phase reactor as the seventh amino acid introduced, the compounds corresponding to L-Trp as $X_8$ in the generic formula, supra, are produced. Similarly by omitting the N-terminal Boc-Ala-Gly-OH group or by introducing a lower alkanoic acid, Boc-Gly-Gly-Gly-OH, Boc-Ala-D-Ala-OH, or p-Glu-OH into the solid phase reactor as the thirteenth amino acid moiety in lieu of the illustrated Boc-Ala-Gly-OH group, there is obtained the corresponding polypeptide variables on the Cys³ group. The fully protected intermediate containing the L-Trp⁸ unit, corresponding to the illustrative compound prepared in the following examples is:

tert-butyloxycarbonyl-L-alanyl-glycyl-S-p-methoxy-benzyl-L-cysteinyl-Nε-(2-chlorobenzyloxycarbonyl)-L-lysyl-D-alanyl-L-phenylalanyl-L-phenylalanyl-L-tryptophyl-Nε-(2-chlorobenzyloxycarbonyl)-L-lysyl-O-benzyl-L-threonyl-L-phenylalanyl-O-benzyl-L-threonyl-O-benzyl-L-seryl-3,4-dimethylbenzyl-L-cysteinyl-methylated-polystyrene resin.

EXAMPLE 1 t-Butyloxycarbonyl-L-alanylglycyl-S-p-methoxybenzyl-L-cysteinyl-N-ε-(2-chlorobenzyloxycarbonyl)-L-lysyl-D-alanyl-L-phenylalanyl-L-phenylalanyl-D-tryptophyl-Nε-(2-chlorobenzyloxycarbonyl)-L-lysyl-O-benzyl-L-threonyl-L-phenylalanyl-O-benzyl-L-threonyl-O-benzyl-L-seryl-3,4-dimethylbenzyl-L-cysteinyl methylated polystyrene resin To a 3 liter reaction vessel is added t-Boc-3,4-dimethylbenzyl-L-cysteine methylated polystyrene resin (240 g., 180 mmoles) having a substitution of 0.75 mmoles amino acid/g resin. The above substituted resin was prepared by the method of B. F. Gisin, *Helvetica Chemica Acta*, 56, 1476 (1973). The resin was then treated in the following manner:

1. methanol (twice);
2. methylene chloride (twice);
3. 5 minute prewash with 1:1 trifluoroacetic acid-methylene chloride (v/v) containing 0.5% dithioerythritol;
4. two consecutive 15 minute treatments with the above described trifluoroacetic acid;
5. methylene chloride (twice);
6. dimethylformamide (twice);
7. two 10 minute treatments with 15% triethylamine in dimethylformamide;
8. dimethylformamide (three times);
9. 20 minute methylene chloride wash;
10. methanol (twice; and
11. methylene chloride (twice).

A contact time of 5 minutes was allowed for each wash unless otherwise indicated.

The resin was gently stirred with t-Boc-O-benzyl-L-threonyl-O-benzyl-L-serine (175 g., 360 mmoles in dimethylformamide containing 55.1 g., 360 mmoles of 1-hydroxybenzotriazole) and 360 ml. of 1 M dicyclohexylcarbodiimide (DCC) in methylene chloride. After stirring overnight the peptide-resin was washed successively with dimethylformamide, methanol, methylene chloride (three times each). To test for completeness of reaction the peptide resin was subjected to a ninhydrin color test following the procedure of E. Kaiser, et al., *Analytical Chemistry*, 34, 595 (1970) and found to be negative. A 2.5 portion of peptide resin was removed and the synthesis continued.

Removal of the t-Boc-α-amino protecting group was carried out as described in steps (3) through (11) above.

The following amino acid residues were introduced consecutively: t-Boc-L-Phenylalalanine (63.6 g., 240 mmoles in 1:1 methylene chloride-dimethylformamide, 240 mmoles DCC). An 8.5 portion of peptide bound resin was removed at the completion of the cycle and the synthesis continued with the addition of t-Boc-O-benzyl-L-threonine (74.2 g., 240 mmoles, in 1:1 methylene chloride-dimethylformamide, 240 mmoles DCC). After washing the resin the synthesis was continued on a 15 g. sample of the pentapeptide resin. The following amino acid residues were further introduced: t-Boc-Nε-(2-chlorobenzyloxycarbonyl)-L-lysine (12.5 g., 30 mmoles in methylene chloride, 33 mmoles DCC), t-Boc-D-tryptophan (9.1 g., 30 mmoles in dimethylformamide, 33 mmoles DCC), t-Boc-L-phenylalanine (7.95 g., 30 mmoles in methylene chloride, 33 mmoles DCC). After washing the resin was dried (17.0 g.) and the synthesis continued on a 5.0 g. portion of the nonapeptide resin with the addition of the following amino acid residues:

t-Boc-D-alanine (1.7 g., 9 mmoles in methylene chloride, 10 mmoles DCC), t-Boc-Nε-(2-chlorobenzyloxycarbonyl)-L-lysine (3.72 g., 9 mmoles in methylene chloride, 10 mmoles DCC), t-Boc-S-p-methoxybenzyl-L-cysteine (3.1 g., 9 mmoles in methylene chloride, 10 mmoles DCC), t-Boc-L-alanylglycine (2.2 g., 9 mmoles in methylene chloride, 10 mmoles DCC). The reaction time for each coupling was 18 hours. Following each coupling the peptide resin was washed as described above. Removal of the α-amino protecting group (t-Boc) at each step was performed as described for the deprotection of t-Boc-3,4-dimethylbenzyl-L-cysteine resin (steps 3–11). After the final washing the resin was dried in vacuo to yield 5.5 g.

EXAMPLE 2

L-Alanylglycyl-L-cysteinyl-L-lysyl-D-alanyl-L-phenylalanyl-L-phenylalanyl-D-tryptophyl-L-lysyl-L-threonyl-L-phenylalanyl-L-threonyl-L-seryl-L-cysteine cyclic (3→14)-disulfide, triacetate The above described preparation from Example 1 (5.5 g.) was treated in vacuo with anhydrous liquid hydrogen fluoride (100 ml.) and anisole (10 ml.) at 0° for 45 minutes. The hydrogen fluoride and anisole were removed under reduced pressure and the residue suspended in anhydrous ether and filtered. The residue was then suspended in 2 N acetic acid (200 ml.), filtered and further washed with water (500 ml.). The aqueous filtrates were combined, diluted with water (6.0 liter) and the pH adjusted to 6.8 with ammonium hydroxide. The solution was titrated with potassium ferricyanide (0.005 N) until a permanent yellow color was observed and stirred for 30 min. After adjustment of the pH to 5 with glacial acetic acid 15 g. of Bio-Rex AG3-X4A (chloride form) resin was added and stirred for 30 min. The resin was filtered and the filtrate lyophilized, 2.1 g.

EXAMPLE 3

Purification and characterization of L-alanylglycyl-L-cysteinyl-L-lysyl-D-alanyl-L-phenylalanyl-L-phenylalanyl-D-tryptophyl-L-lysyl-L-threonyl-L-phenylalanyl-L-threonyl-L-seryl-L-cysteine cyclic (3→14)-disulfide, triacetate The above titled crude product was purified as follows:

2.1 g. of material was dissolved in a minimum amount of 2 N acetic acid and applied to a column (2.5×200 cm.) of Sephadex G-25 (fine) in 2 N acetic acid. The column effluent was monitored by the Folin-Lowry color reaction on every third fraction (99 drops each). Fractions 175–197 were combined and lyophilized to yield 115 mg. of product. The material was shown to be homogenous by thin layer chromatography systems 4:1:5 (n-butanol:acetic acid:water) and 7:7:6 (isoamyl alcohol:pyridine:water). Thin layer chromatograms were visualized with iodine and chlorine peptide reagent. Amino acid anlaysis in 4 N methane sulfonic acid:

Ser, 0.98; Thr, 1.82; Gly, 1.00; Ala, 2.09; Cys, 1.84; Phe, 2.87; Lys, 1.89; Trp, 0.75.

EXAMPLE 4

The activity of the product of the preceding preparatory example, (D-Ala$^5$, D-Trp$^8$)-Somatostatin, was determined by the following procedure:

Albino male rats were administered Nembutal intraperitoneally at a dose of 50 milligrams per kilogram. Fifteen minutes later a subcutaneous injection of the test compound or physiological saline was administered. Ten minutes later 0.5 milliliters of arginine (300 milligrams per milliliter, pH 7.2) is injected into the heart. Five minutes after receipt of the arginine the rats are decapitated and blood is collected into trasylol-EDTA. An appropriate aliquot was assayed for growth hormone, insulin and glucagon by radioimmunoassay. The results of the assay are as follows:

| Compound | Dose ug/kg | GH ng/ml | Insulin μU/ml | Glucagon pg/ml | No. of Animals |
|---|---|---|---|---|---|
| (D-Ala$^5$, D-Trp$^8$)-Somatostatin | 1,000 | 34 ± 5 | 42 ± 5 | 40 ± 6 | 10 |
| Control | — | 312 ± 63 | 191 ± 11 | 42 ± 3 | |
| (D-Ala$^5$, D-Trp$^8$)-Somatostatin | 100 | 117 ± 31 | 68 ± 11 | 53 ± 11* | 10 |
| Control | — | 526 ± 153 | 339 ± 45 | 39 ± 7 | |
| (D-Ala$^5$, D-Trp$^8$)-Somatostatin | 10 | 53 ± 6 | 215 ± 13 | 78 ± 7* | 10 |
| Control | — | 254 ± 40 | 321 ± 49 | 92 ± 23 | |
| (D-Ala$^5$, D-Trp$^8$)-Somatostatin | 200 | 50 ± 3 | 174 ± 13 | 39 ± 6 | |

*not significant

The results show that (D-Ala$^5$, D-Trp$^8$)-Somatostatin, representative of the other compounds of the invention, is an effective agent for reducing secretion of growth hormone and insulin without materially affecting glucagon levels.

The compounds described herein may be administered to warm-blooded mammals, including humans, either intravenously, subcutaneously, intramuscularly, or orally to inhibit the hypersecretion of growth hormone, such as in acromegaly, or to inhibit the hypersecretion of insulin, such as in insulinoma. The required dosage will vary with the particular condition being treated, the severity of the condition and the duration of treatment.

The active ingredient may be administered alone or in combination with pharmaceutically acceptable carriers or excipients. Suitable pharmaceutical compositions will be apparent to those skilled in the art.

What is claimed is:

1. The polypeptide which is L-alanyl-glycyl-L-cysteinyl-L-lysyl-D-alanyl-L-phenylalanyl-L-phenylalanyl-D-tryptophyl-L-lysyl-L-threonyl-L-phenylalanyl-L-threonyl-L-seryl-L-cysteine or a non-toxic acid addition salt thereof.

2. The polypeptide which is L-alanyl-glycyl-L-cysteinyl-L-lysyl-D-alanyl-L-phenylalanyl-L-phenylalanyl-D-tryptophyl-L-lysyl-L-threonyl-L-phenylalanyl-L-threonyl-L-seryl L-cysteine (cyclic 3→14)-disulfide or a non-toxic acid addition salt thereof.

* * * * *